United States Patent
Reynolds

(10) Patent No.: US 7,097,847 B2
(45) Date of Patent: Aug. 29, 2006

(54) PROCESS TO PREPARE A SKIN SOFTENING COMPOSITION

(76) Inventor: Grant Reynolds, 6174 Coolihans Sdrd., Caledon East, ON (CA) L0N 1E0

( * ) Notice: Subject to any disclaimer, the term of this patent is extended or adjusted under 35 U.S.C. 154(b) by 109 days.

(21) Appl. No.: 10/823,884

(22) Filed: Apr. 14, 2004

(65) Prior Publication Data

US 2004/0241199 A1    Dec. 2, 2004

Related U.S. Application Data

(60) Provisional application No. 60/468,302, filed on Apr. 14, 2003.

(51) Int. Cl.
  *A61K 6/00*   (2006.01)
  *A61K 8/02*   (2006.01)
  *A61K 31/74*  (2006.01)
  *A61K 8/00*   (2006.01)
  *A61K 8/18*   (2006.01)

(52) U.S. Cl. .................... 424/401; 424/69; 424/59; 424/78.03

(58) Field of Classification Search ................. 424/401
  See application file for complete search history.

(56) References Cited

U.S. PATENT DOCUMENTS

| 4,387,382 | A  | * | 6/1983  | Kohashi ................ 347/55   |
| 5,976,555 | A  | * | 11/1999 | Liu et al. ............. 424/401  |
| 6,150,403 | A  | * | 11/2000 | Biedermann et al. ... 514/460    |
| 6,214,318 | B1 | * | 4/2001  | Osipow et al. ........ 424/45    |

* cited by examiner

*Primary Examiner*—Carlos A. Azpuru
*Assistant Examiner*—David Vanik

(57) ABSTRACT

This invention provides an industrially advantageous process for preparing a composition containing urea and salicylic acid in a water-washable ointment of a non-aqueous emulsion type that exfoliates and moisturizes skin.

24 Claims, No Drawings

PROCESS TO PREPARE A SKIN SOFTENING COMPOSITION

CROSS-REFERENCE TO RELATED APPLICATION

This application claims priority under 35 USC 119(e) from U.S. Provisional Patent Application No. 60/468,302, having Grant Reynolds as inventor, filed Apr. 14, 2003, and titled "PROCESS TO PREPARE SKIN SOFTENING OINTMENT", which is incorporated by reference herein for all purposes.

BACKGROUND

Many commercial products are available for treatment of dry, rough skin. The active ingredients in these products include humectants, emollients, keratolytics and occlusives. Urea, salicylic acid and white petrolatum are all known as ingredients in commercially available topical products. Urea is used in topical compositions as an emollient, humectant as well as a keratolytic. Because urea is naturally present in the stratum corneum, it is considered a natural moisturizing factor. Salicylic acid possesses keratolytic activity. White petrolatum is a hydrocarbon base that is used in ointments; it also has the additional value of being an emollient and an occlusive.

Despite their widespread use, there are significant problems with skin products that contain urea and salicylic acid. Urea is not stable in an aqueous environment, and breaks down into carbon dioxide and ammonia, with the concomitant formation of an unpleasant smell. In contrast, urea is stable in non-aqueous bases, such as hydrocarbons. However, non-aqueous bases are hydrophobic and uncomfortable to the touch, i.e. feel sticky. Additionally, these non-aqueous bases do not wash off the skin easily. The physical unpleasantness of these bases decreases patient compliance and the effectiveness of compositions that contain urea. Moreover, the salicylic acid particles are known to crystallize and localize during the shelf life of commercially available products. The non-uniformity of the salicylic acid crystals necessitated an additional step of remixing the product in order to maintain a uniform product during the shelf life of the product.

We have discovered a process to create a stable, uniform composition, with no crystal growth, comprising urea and salicylic acid in a white petrolatum base.

SUMMARY OF THE INVENTION

This invention provides an industrially advantageous process for preparing a composition containing urea and salicylic acid in a water-washable ointment of a non-aqueous emulsion type that exfoliates and moisturizes skin.

In one embodiment, the skin softening composition is prepared by the steps of (a) heating and mixing a humectant and a non-aqueous thickener under vacuum in a first vessel; (b) introducing urea under vacuum into the mixture of step (a); (c) heating and mixing the contents of step (b) under vacuum, at a temperature sufficient to dissolve the urea; (d) heating and mixing a non-aqueous base and at least one emulsifier in a second vessel, whereby the non-aqueous base liquefies; (e) drawing by vacuum the mixture from step (d) into the mixture in the first vessel; (f) mixing, heating and homogenizing and the contents of step (e) under vacuum; (g) cooling, mixing and homogenizing the mixture of step (f) to a congealing temperature under vacuum; (h) cooling the mixture of step (g); (i) drawing by vacuum salicylic acid into the mixture of step (h); (j) recirculating the mixture of step (i) under vacuum; and, (k) cooling the mixture of step (j) under vacuum.

In another embodiment, the skin softening composition is prepared by the steps of: (a) heating and mixing glycerol and PEG-8 under vacuum in a first vessel; (b) introducing urea under vacuum into the mixture of step (a); (c) heating and mixing the contents of step (b) under vacuum, at a temperature sufficient to dissolve the urea; (d) heating and mixing white petrolatum, polysorbate 80, PEG 40 sorbitan peroleate and polyoxyl 40 stearate in a second vessel whereby the white petrolatum liquefies; (e) drawing by vacuum the mixture from step (d) into the first mixture of the first vessel; (f) mixing, heating and homogenizing the contents of step (e) under vacuum; (g) cooling, mixing and homogenizing mixture of step (f) to a congealing temperature under vacuum; (h) cooling the mixture of step (g); (i) drawing by vacuum salicylic acid into the mixture from step (h); (j) recirculating the mixture of step (i) under vacuum; and (k) cooling and mixing the mixture of step (j) under vacuum.

In a third embodiment, the skin softening composition may be prepared as follows: (a) in step (a) the heating is at a temperature of about 80° C. to about 84° C., the mixing is at a speed of about 18 rpm and the vacuum is at about −400 mbar; (b) in step (d) the heating is at a temperature of about 63° C. to about 67° C. and the mixing is at a speed such that a vortex is not formed; (e) in step (c) the heating is at a temperature of about 80° C. to about 84° C., the mixing is at a speed of about 36 rpm and the vacuum is at about −400 mbar; (f) in step (e) the vacuum-drawing is at a vacuum of about −200 mbar, the mixing is at a speed of about 36 rpm; (g) in step (f) the mixing is at a speed of about 36 rpm, the heating is at a temperature of about 80° C. to about 84° C., the vacuum is at about −400 mbar, the homogenizing is at a speed of 17 RPM and the duration of the mixing and heating is about 18 to about 22 minutes; (h) in step (g) the cooling the mixture is cooled to a range of about 43° C. to about 47° C., the mixing is at a speed of about 36 rpm, the homogenizing is at a speed of about 1700 rpm, and the vacuum is at about −400 mbar; (i) in step (h) the mixture is cooled to a range of about 29° C. to about 40° C. and the vacuum is at about −400 mbar; (j) in step (i) the vacuum is at about −750 mbar and the mixing is at about 36 rpm; (k) in step (j) the recirculating and mixing is conducted for about 38 to about 42 minutes and the vacuum is at about −600 mbar; and (i) in step (k) the mixing is at a speed of about 36 rpm, the vacuum is at about −600 mbar and the mixture is cooled to a range of about 23° C. to about 27° C.

The method according to this embodiment produces a skin softening composition having the following formula: (a) about 49.35% white petrolatum; (b) about 0.9% polysorbate 80; (c) about 6.1% PEG-40 Sorbitan Peroleate; (d) about 3.65% polyoxyl 40 stearate; (e) about 11% glycerol; (f) about 14% PEG-8; (g) about 10% urea and, (h) about 5% salicylic acid.

DESCRIPTION OF THE INVENTION

The present invention relates to a process for preparing a stable, uniform, water-washable ointment of a non-aqueous emulsion. The composition is comprised of (i) about 49.35% (w/w) of white petrolatum, (ii) about 0.9% (w/w) of polysorbate 80, (iii) about 6.1% (w/w) of PEG 40 sorbitan peroleate, (iv) about 3.65% (w/w) of polyoxyl 40 stearate, (v) about 11.0% (w/w) of glycerol, (vi) about 14.0% (w/w) of PEG-8, (vii) about 10.0% (w/w) of urea, and (viii) about 5.0% (w/w) of salicylic acid.

The water-washable ointment of a non-aqueous emulsion type of the present invention may be used to treat corns, calluses and areas of thickened dry skin. The active pharmaceutical agents of the present composition are about 10% urea and about 5% salicylic acid. Urea can be used in concentrations of up to about 20%, salicylic acid can be used in concentrations of up to 20%.

Stable pharmaceutical suspensions are physically and chemically stable during the shelf life of the composition. Shelf life may range from 6 months to 5 years. The process of this application provides a suspension that is stable, i.e., does not separate during storage. Salicylic acid crystals do not migrate out of the ointment, creating an unstable preparation. Urea in the suspension does not break down into carbon dioxide and ammonia and no unpleasant smell is produced. In addition to the good sedimentation properties, the suspension remains uniform during storage, that is the component ingredients do not fall out of the suspension over time.

The water-free lipid base of the composition has the addition of hydrophillic emulsifiers that lead to a better disposition of the urea and salicylic acid for the treatment of dry, thickened skin. The emulsifiers add to the unique washable property of the composition in that the composition may be washed off the skin without the use of soaps or synthetic detergents. This is significant in the treatment of dry skin where use of soaps and detergents is contraindicated.

The topical composition may be a semi-solid at room temperature but is easily absorbed into the stratum corneum. Such a composition can include petroleum-based liquids and solid fractions as skin protectants. The solid skin protectant can be present at concentration of up to about 50% of the compositions; protectants may include petrolatum or semi-synthetic hydrocarbons of the same nature as petrolatum. Mixtures of such ingredients may also be used. Liquid skin protectants can be petrolatum in the composition up to about 50% (w/w) of the composition and include a synthetic or semi-synthetic oleaginous liquid fraction. The liquid skin protectant can be mineral oil, which is a liquid mixture of hydrocarbon obtained from petroleum.

The process of the invention may include humectants. Glycerol, propylene glycol, sorbitol and triacetin can be used as the humectant and base component necessary for the discontinuous phase of the composition. Bases that are humectants have the additional benefit of hydrating the stratum corneum. The humectant can be present in the composition up to about 15% (w/w). In one embodiment, glycerol is present in the composition at about 11% (w/w).

The humectant is mixed with a non-aqueous thickener. The non-aqueous thickener is selected from the group consisting of polyethylene glycol, hydroxyethyl cellulose, hydroxypropyl cellulose, carboxyvinyl polymers, acacia, tragcanth, synthetic and non-synthetic gums and mixtures thereof. In one embodiment, PEG-8 is used in the method to prepare the skin softening ointment.

Various emulsifiers may be used in the process to prepare the composition of this invention. To increase the water solubility of some emulsifiers, polyoxyethylene groups are added through an ether linkage with one of their alcohol groups. The most widely used compounds are the polyoxyethylene sorbitan fatty acid esters. Closely related compounds include polyoxyethylene glyceryl and polyoxypropylene esters. It is also possible to have a direct ether linkage with the hydrophobic group as with a polyoxyethylene-stearyl ether or a polyoxyethylene-alkyl phenol. Other useful emulsifiers include acacia, tragcanth, oleic acid, stearic acid, cetyl stearyl alcohol, cetyl alcohol, lanolin, mineral oil, anionic emulsifying wax, polyethoxylated castor oil, hydroxypropyl cellulose, diethanolamine, polyxyethylene ether, monostearate glyceryl, lecithin, medium chain triglycerides, methyl cellulose, monoethanolamine, nonionic emulsifying wax, oleic acid, poloxamer, polyethyoxylated castor oil, polyoxyethylene ethers, polyoxyethylene fatty acid esters, polyoxyethylene stearates, propylene glycol alginate, sodium citrate, sodium lauryl sulfate, sodium phosphate monobasic, sorbitan fatty acid esters, stearic acid, triethanolamine, medium chain triglycerides and mixtures thereof.

The composition can also contain known adjuvants and additives, such as bactericides, fungicides, virucides, light filter substances, active ingredients with a cooling action, antioxidants, plant extracts, antiinflammatories, substances which promote wound healing, skin-lightening agents, screening agents, odor absorbers, skin-coloring agents screening agents, odor absorbers, skin-coloring agents, perfumes, antifoams, dyes, pigments which have a coloring action, thickeners, surface-active substances, emulsifiers, emollients, moisturizers and/or humectants, fats, oils, waxes, alcohols, polyols, polymers, foam stabilizers, electrolytes, organic solvents, silicone derivatives or chelating agents.

The process to prepare the composition is an anhydrous method; that is, it has no water in the process. Prior to the steps involved in the process, the mixing vessel is placed under a vacuum of up to $-1000$ mbar to displace all water out of the system. The process that is described herein provides for a water-washable semisolid, nonaqueous emulsion ointment. The resulting salicylic acid/urea product is highly occlusive and highly water-washable. The process is used to prepare an anhydrous emulsion comprised of a non-aqueous base, at least one emulsifier and a humectant and a non-aqueous thickener.

The process for the preparation of the composition involves heating and mixing the humectant and a non-aqueous thickener under vacuum in a first vessel. The temperature of the vessel is set at about 55° C. to about 100° C., or at about 80° C. to about 90° C., or at about 80° C. to about 84° C. The mixing speed is set at a medium speed, at about 15 to about 45 RPM, preferably at about 36 RPM. A high vacuum is set, at about $-200$ to about $-999$ mbar, preferably at about $-350$ to about $-450$ mbar, preferably at about $-400$ mbar. High vacuum and heat draw the white crystal pellets of urea, which is at room temperature, into the vessel. The urea is allowed to dissolve in the mixture. When the urea is dissolved, the heating is stopped.

In a second vessel, the mixture of a non-aqueous base and at least one emulsifier are heated at a temperature a temperature of about 35° C. to about 55° C., more preferably from 40° C. to about 50° C., most preferably from 43° C. to about 47° C. The mixture is mixed at a speed where a vortex does not form. The mixture from the first vessel is added to the mixture of the second vessel at a temperature, of about 70° C. to about 100° C., preferably at about 80° C. to about 90° C., preferably at about 80° C. to about 84° C. The vacuum is set, at about $-200$ mbar to about $-999$ mbar, more preferably at about $-350$ to about $-450$ mbar, most preferably at about $-400$ mbar. The mixture is mixed at high speed of about 15 to about 45 RPM, most preferably at about 36 RPM. The homogenizer is also turned to a high speed of about 1200 to 2000 RPM, more preferably 1500 to 1800

RPM, most preferably at about 1700 RPM. The slow addition and high speed mixing and homogenizing allows for a phase inversion of the continuous/discontinuous phases.

The mixture is then mixed at a speed of about 15 to about 45 RPM, most preferably at about 36 RPM and homogenized at a speed of about 1200 to 2000 RPM, more preferably 1500 to 1800 RPM, most preferably at about 1700 RPM. The high temperature of the vessel is maintained for a period of about 20 minutes. The heating element is then lowered to about 10° C. to about 20° C., and the mixture allowed to cool to about 43° C. to about 47° C. When the batch is cooled to about 43° C. to about 47° C., the homogenizer is turned off. The mixture is allowed to cool further to about 29° C. to about 40° C., while maintaining the high rate of mixing.

Salicylic acid is added by vacuum into cooled mixture. The salicylic acid is a white powder that is milled before adding to avoid the addition of any grit. Recirculation of the mixture is achieved through a recirculating loop built into the mixing vessel that draws the mixture from the bottom of the mixture into the top of the mixture under high vacuum of about −200 mbar to about −999 mbar preferably about −600 mbar. During the recirculation, the composition is being deaerated and dehydrated, allowing for a more stable final product. Deaerating and dehydrating the composition may be achieved through other means.

The process of the present invention optimizes the use of temperature and vacuum to minimize moisture which results in the degradation urea, and the resultant unwanted byproducts of ammonia and carbon dioxide and the concomitant formation of an unpleasant smell.

An example of the process for preparing the composition is described below. The example is purely illustrative without any intention of being limiting. It is to be understood that the invention is not limited in its application to the details of construction and the arrangement of the components set forth in the following description. The invention includes other embodiments and can be practiced and implemented in various ways. It is also to be understood that the phraseology and terminology employed herein is for the purpose of description only and should not be regarded as limiting.

EXAMPLE I 493.5 Kg of white petrolatum, 9.0 Kg of polysorbate 80, 61.0 Kg of PEG-40 Sorbitan Peroleate, 36.5 Kg Polyoxyl 40 Stearate were added to a 750 L preparatory vessel add. The vessel temperature was set to 65° C. When the white petrolatum phase began to liquefy, a Lightnin mixer (www.ligtnin-mixer.com) was used to mix the materials to facilitate the melting of the raw materials. No vortex was created. When the temperature reached approximately 65° C., the temperature was set and mixing continued until the material melted.

At the same time a Ross 1000 L mixing vessel (Charles Ross and Son Company, Hauppauge, N.Y.; www.mixers.com) was prepared by applying a high vacuum of up to about −800 mbar. 105.0 Kg glycerin and 140.0 Kg PEG-8 were added to the 1000L mixer and mixed at 18 rpm. The Ross mixing vessel vacuum was set to 40 mbar dynamic vacuum and the temperature set to 82° C. 100.0 Kg of urea and 5.0 Kg of glycerin were immediately drawn into the vessel by the vacuum. The mixer speed was increased to 36 rpm.

When the urea was dissolved, the mixture was slowly transferred to the white petrolatum mixture in the mixing vessel the vacuum set point was decreased to 200 rpm and the mixer speed increased to 36 RPM. No air was drawn into the batch. The set point temperature was maintained at 82° C. The mixing continued for approximately 20 minutes. At the end of 20 minutes, the set point temperature was changed to 10° C. the batch cooled to approximately 45° C. and the mixture began to congeal. Congealing is defined as the change from a fluid to a solid state. The mixture was homogenized in the Ross mixing vessel at a high speed, about 1700 RPM. When the batch reached approximately 37° C. the set point temperature was turned off. During the cooling/homogenizing of this step, 50.0 Kg of salicylic acid was weighed out and passed through a Comil (225 spacers, 032 screen) (Quadro Engineering Company, Kitchener Ontario, Canada) into a stainless steel container.

While the mixing speed was maintained at 36 RPM, salicylic acid was added into the mixing vehicle through a hose. The vacuum set point was increased to −850 mbar for approximately 7 minutes, and then the vacuum was reset to a set point of −600 mbar. The mixture was recirculated through a loop that pumped the mixture from the bottom of the vessel up through the top of the vessel, under vacuum The batch was mixed and reciculated for approximately 40 minutes. The mixer, recirculating pump and vacuum were shut off and the mixing vessel scrapped down. The vacuum was set to −600 mbar, the mixer speed to set to 36 RPM and the temperature to 25° C. The mixture was mixed for approximately 12 minutes. When the temperature reached 25° C., mixing was continued for approximately 5 minutes, and then the mixture was shut off, and the vacuum was slowly released.

What I claim is:

1. An anhydrous method of making a skin softening ointment, comprising the steps of:
   (a) heating and mixing a humectant and a non-aqueous thickener under vacuum in a first vessel;
   (b) introducing urea under vacuum into the mixture of step (a);
   (c) heating and mixing the contents of step (b) under vacuum, at a temperature sufficient to dissolve the urea;
   (d) heating and mixing a non-aqueous base and at least one emulsifier in a second vessel, whereby the non-aqueous base liquefies;
   (e) drawing by vacuum the mixture from step (d) into the mixture in the first vessel;
   (f) mixing, heating and homogenizing and the contents of step (e) under vacuum;
   (g) cooling, mixing and homogenizing the mixture of step(f) to a congealing temperature under vacuum;
   (h) cooling the mixture of step (g);
   (i) drawing by vacuum salicylic acid into the mixture of step (h);
   (j) recirculating the mixture of step (i) under vacuum; and,
   (k) cooling the mixture of step (j) under vacuum.

2. The method of claim 1, wherein the humectant is selected from the group consisting of glycerol, propylene glycol, sorbitol and triacetin and mixtures thereof.

3. The method of claim 1, wherein the non-aqueous base is selected from the group consisting of mineral oil, petrolatum and lanolin, grapeseed oil, propylene glycol, and beeswax and mixtures thereof.

4. The method of claim 1, wherein the emulsifier is selected from the group consisting of acacia, oleic acid, stearic acid, cetearyl alcohol, cetyl alcohol, lanolin, mineral oil, anionic emulsifying wax, polyethoxylated castor oil, hydroxypropyl cellulose, diethanolamine, polyxyethylene ether, monostearate glyceryl, lecithin, medium chain triglycerides, methyl cellulose, monoethanolamine, nonionic emulsifying wax, oleic acid, poloxamer, polyethyoxylated castor oil, polyoxyethylene ethers, polyoxyethylene fatty acid esters, polyoxyethylene stearates, propylene glycol aldginate, sodium citrate, sodium lauryl sulfate, sodium phosphate monobasic, sorbitan fatty acid esters, stearic acid, triethanolamine, medium chain triglycerides and mixtures thereof.

5. The method of claim 4, wherein the emulsifier is selected from the group consisting of polyoxyethylene sorbitan fatty acid esters, polyoxyethylene glyceryl, polyoxypropylene esters, polyoxyethylene-stearyl ether, polyoxyethylene-alkyl phenol and mixtures thereof.

6. The method of claim 1, wherein the non-aqueous thickener is selected from the group consisting of polyethylene glycol, hydroxyethyl cellulose, hydroxypropyl cellulose, polyethylene oxide, carboxyvinyl polymers, acacia, tragcanth, synthetic and nonsynthetic gums and mixtures thereof.

7. The method of claim 6, wherein the non-aqueous thickener is PEG-8.

8. The method of claim 1, wherein the amount of urea added is up to about 20% (w/w).

9. The method of claim 8, wherein the amount of urea added is about 10% (w/w).

10. The method of claim 1, wherein the amount of salicylic acid is up to about 20% (w/w).

11. The method of claim 10, wherein the amount of salicylic acid is about 5% (w/w).

12. The method of claim 1, wherein the temperature of heating in step (d) is a range from about 63° C. to about 67° C. and the mixing is at a speed wherein a vortex is not formed.

13. The method of claim 1, wherein the temperature of heating in step (a) is a range of about 80° C. to about 84° C., the mixing is at a speed of about 18 rpm and the vacuum is at about −400 mbar.

14. The method of claim 1, wherein the temperature of heating in step (c) is a range of about 80° C. to about 84° C., the mixing is at a speed of about 36 rpm and the vacuum is at about −400 mbar.

15. The method of claim 1, wherein the drawing under vacuum in step (e) is at about −200 mbar, the mixing is at a speed of about 36 rpm.

16. The method of claim 1, wherein in mixing in step (f) is at a speed of about 36 rpm, the heating is a range from about 80° C. to about 84° C., the vacuum is at about −400 mbar, the homogenizing is at a speed of 1700 RPM and the duration of the mixing, and heating is about 18 to about 22 minutes.

17. The method of claim 1, wherein the mixture in step (g) is cooled to a range of about 43° C. to about 47° C., the mixing is at a speed of about 36 rpm, the homogenizing is at a speed of about 1700 rpm, and the vacuum is at about −400 mbar.

18. The method of claim 1, wherein the mixture in step (h) is cooled to a range of about 29° C. to about 40° C. and the vacuum is at about −400 mbar.

19. The method of claim 1, wherein the vacuum drawing in step (i) is under a vacuum of about −750 mbar and the mixing is at about 36 rpm.

20. The method of claim 1, wherein the recirculation in step (j) is conducted for about 38 to about 42 minutes and the vacuum is at about −600 mbar.

21. The method of claim 1, wherein the mixing in step (k) is at a speed of about 36 rpm, the vacuum is at about −600 mbar and the mixture is cooled to a range of about 23° C. to about 27° C.

22. An anhydrous method of making a skin softening ointment comprising the following steps:
   (a) heating and mixing glycerol and PEG-8 under vacuum in a first vessel;
   (b) introducing urea under vacuum into the mixture of step (a);
   (c) heating and mixing the contents of step (b) under vacuum, at a temperature sufficient to dissolve the urea;
   (d) heating and mixing white petrolatum, polysorbate 80, PEG 40 sorbitan peroleate and polyoxyl 40 stearate in a second vessel whereby the white petrolatum liquefies;
   (e) drawing by vacuum the mixture from step (d) into the first mixture of the first vessel;
   (f) mixing, heating and homogenizing the contents of step (e) under vacuum;
   (g) cooling, mixing and homogenizing mixture of step (f) to a congealing temperature under vacuum;
   (h) cooling the mixture of step (g);
   (i) drawing by vacuum salicylic acid into mixture from step (h);
   (j) recirculating the mixture of step (i) under vacuum; and
   (k) cooling and mixing the mixture of step (j) under vacuum.

23. The method of claim 22 wherein:
   in step (a) the heating is at a temperature of about 80° C. to about 84° C., the mixing is at a speed of about 18 rpm and the vacuum is at about −400 mbar;
   in step (d) the heating is at a temperature of about 63° C. to about 67° C. and the mixing is at a speed such that a vortex is not formed;
   in step (c) the heating is at a temperature of about 80° C. to about 84° C., the mixing is at a speed of about 36 rpm and the vacuum is at about −400 mbar;
   in step (e) the vacuum-drawing is at a vacuum of about −200 mbar, the mixing is at a speed of about 36 rpm;
   in step (f) the mixing is at a speed of about 36 rpm, the heating is at a temperature of about 80° C. to about 84° C., the vacuum is at about −400 mbar, the homogenizing is at a speed of 17 RPM and the duration of the mixing and heating is about 18 to about 22 minutes;
   in step (g) the cooling the mixture is cooled to a range of about 43° C. to about 47° C., the mixing is at a speed of about 36 rpm, the homogenizing is at a speed of about 1700 rpm, and the vacuum is at about −400 mbar;
   in step (h) the mixture is cooled to a range of about 29° C. to about 40° C. and the vacuum is at about −400 mbar;
   in step (i) the vacuum is at about −750 mbar and the mixing is at about 36 rpm;
   in step (j) the recirculating and mixing is conducted for about 38 to about 42 minutes and the vacuum is at about −600 mbar;
   in step (k) the mixing is at a speed of about 36 rpm, the vacuum is at about −600 mbar and the mixture is cooled to a range of about 23° C. to about 27° C.

24. The method of claim 23 to provide a skin softener comprising
   a. about 49.35% white petrolatum;
   b. about 0.9% polysorbate 80;
   c. about 6.1% PEG-40 Sorbitan Peroleate;
   d. about 3.65% polyoxyl 40 stearate;
   e. about 11% glycerol;
   f. about 14% PEG-8;
   g. about 10% urea; and
   h. about 5% salicylic acid.

* * * * *